United States Patent
Suga et al.

(10) Patent No.: US 7,141,359 B2
(45) Date of Patent: *Nov. 28, 2006

(54) DEVELOPERS FOR THERMAL RECORDING MATERIALS AND THERMAL RECORDING MATERIALS

(75) Inventors: Mamoru Suga, Osaka (JP); Kaori Suzuki, Fukuoka (JP); Yoshihide Kimura, Tokyo (JP); Naomi Sumikawa, Tokyo (JP)

(73) Assignees: API Corporation, Osaka (JP); Nippon Paper Industries, Co., Ltd., Tokyo (JP)

(*) Notice: Subject to any disclaimer, the term of this patent is extended or adjusted under 35 U.S.C. 154(b) by 90 days.

This patent is subject to a terminal disclaimer.

(21) Appl. No.: 10/362,896

(22) PCT Filed: May 31, 2002

(86) PCT No.: PCT/JP02/05351

§ 371 (c)(1),
(2), (4) Date: Mar. 6, 2003

(87) PCT Pub. No.: WO02/098674

PCT Pub. Date: Dec. 12, 2002

(65) Prior Publication Data

US 2005/0118526 A1   Jun. 2, 2005

(30) Foreign Application Priority Data

Jun. 1, 2001  (JP) .............................. 2001-167233
Sep. 28, 2001  (JP) .............................. 2001-301577

(51) Int. Cl.
G03C 1/73 (2006.01)
(52) U.S. Cl. ...................... 430/332; 430/224; 430/243; 430/334
(58) Field of Classification Search ................ 430/224, 430/243, 619, 437, 485, 473, 234, 434, 332, 430/334; 503/224, 243, 201, 209, 255; 658/723, 720; 568/706, 640, 726; 558/412
See application file for complete search history.

(56) References Cited

U.S. PATENT DOCUMENTS

| | | | | |
|---|---|---|---|---|
| 2,730,551 A | * | 1/1956 | Beaver et al. ............... | 568/720 |
| 2,773,907 A | * | 12/1956 | Sullivan et al. ............. | 568/720 |
| 2,783,279 A | * | 2/1957 | Chiddix ...................... | 568/720 |
| 2,849,325 A | * | 8/1958 | Lincoln .................... | 106/194.1 |
| 2,905,737 A | * | 9/1959 | Webb ........................ | 524/342 |
| 3,244,549 A | | 4/1966 | Farnham et al. ........... | 117/36.2 |
| 3,560,229 A | | 2/1971 | Farnham et al. ............ | 106/21 |
| 3,937,864 A | * | 2/1976 | Kohmura et al. ........... | 503/208 |
| 4,282,390 A | * | 8/1981 | McGarry et al. ........... | 568/720 |
| 4,992,596 A | * | 2/1991 | Jeffries et al. .............. | 568/720 |
| 5,242,884 A | * | 9/1993 | Mando et al. ............. | 503/209 |
| 5,372,917 A | | 12/1994 | Tsuchida et al. | |
| 5,474,968 A | | 12/1995 | Norimatsu ................... | 503/226 |
| 5,972,554 A | * | 10/1999 | Nagatsuka et al. ....... | 430/108.1 |
| 6,146,823 A | * | 11/2000 | Katoh ......................... | 430/619 |
| 2004/0241598 A1 | * | 12/2004 | Suga et al. ................. | 430/434 |

FOREIGN PATENT DOCUMENTS

| | | |
|---|---|---|
| EP | 644058 | 3/1995 |
| JP | 40-9309 | 8/1961 |
| JP | 51-13661 | 5/1976 |
| JP | 58-181686 | 10/1983 |
| JP | 58-187394 | 11/1983 |
| JP | 61-175078 | 8/1986 |
| JP | 62-167082 | 7/1987 |

(Continued)

OTHER PUBLICATIONS

3M's Dry Silver Teachnology, 3M Company St. Paul, Minnesota, David A. Morgan, Mar. 1975.*

*Primary Examiner*—Thorl Chea
(74) *Attorney, Agent, or Firm*—Wenderoth, Lind & Ponack, L.L.P.

(57) ABSTRACT

The object of the present invention is to provide a novel developer capable or realizing a thermal recording material superior in preservation stability (i.e., heat resistance, moisture resistance) of color images and non-image areas, while satisfying the recent request for high sensitivity, and a thermal recording material using the developer.

The developer for a thermal recording material of the present invention is characterized in that it consists of a composition containing, of condensates represented by the formula (I):

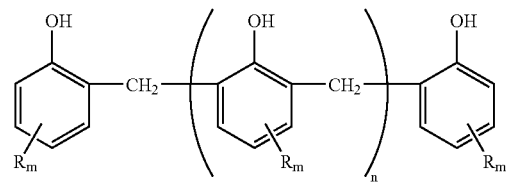

wherein R is a halogen atom, a hydroxyl group, an alkyl group having 1 to 5 carbon atoms, an alkoxyl group having 1 to 5 carbon atoms, a cyano group, a nitro group, an aryl group or an aralkyl group, R in the number of m may be the same or different and m is an integer of 0–3, and n is an integer of 0–3, a condensate having two cores wherein n=0 as a main component, and at least one kind of condensate of the formula wherein n=1–3, and that a thermal recording material obtained using this developer shows high sensitivity, high dynamic color density, and superior preservation stability.

1 Claim, No Drawings

FOREIGN PATENT DOCUMENTS

| | | |
|---|---|---|
| JP | 62-279982 | 12/1987 |
| JP | 62-290579 | 12/1987 |
| JP | 9-278695 | 10/1997 |
| JP | 2001-96926 | 4/2001 |

* cited by examiner

DEVELOPERS FOR THERMAL RECORDING MATERIALS AND THERMAL RECORDING MATERIALS

This application is a U.S. national stage of International Application No. PCT/JP02/05351 filed May 31, 2002.

TECHNICAL FIELD

The present invention relates to a developer for thermal recording material and a thermal recording material.

BACKGROUND ART

In general, a thermal recording material (medium for thermal recording) is obtained by applying a coating liquid onto a support such as paper, plastic film and the like to form a heat coloring layer, wherein the coating liquid is obtained by grinding and dispersing a basic dye, which is colorless or in a pale color at ambient temperature, and an organic developer, to give respective fine particles, mixing them and adding a binder, a filler, a sensitizer, a lubricant, other additive and the like to the mixture. By heating with a thermal head, a thermal pen, a laser light and the like, it affords a developed color record. The basic principle of such recording method is considered to be the change of the dye to have a color upon chemical contact of an electron donative dye with an organic developer. Such recording method (thermal recording method) is characterized in that it is free of the need of complicated treatments such as development, fixing and the like, it can record in a short time using a comparatively economical and simple apparatus, is maintenance free, is free of noise during recording, and the obtained color is very clear, as compared to other recording methods conventionally put to practical use, and has been widely used as a recording material for computer output, printer of electronic calculator and the like, recorder for medical measurement, facsimile, automatic ticket vending machine, label fields, copying machine and the like. As multi-purpose and high performance types of these apparatuses have been progressively provided in recent years, a higher-grade thermal recording material (medium for thermal recording) has been demanded. For high speed recording and miniaturization of apparatuses, for example, the thermal energy of the thermal head of recording apparatuses tends to become very small, and a thermal recording material (medium for thermal recording) to be used therefor is required to show sufficient color density to afford a high density and clear color image even with a very little energy.

To meet such request, various compounds having phenolic hydroxyl group have been proposed as a developer to be contained in a heat coloring layer, and disclosed in, for example, JP-B-40-9309, JP-B-43-4160, JP-B-45-14039, JP-B-51-29830, JP-A-56-144193 and the like. Generally, bisphenol compounds, 4-hydroxybenzoic acid ester and the like have been put to practical use alone or in combination of several kinds thereof. However, the conventional materials such as these are associated with problems of, for example, low thermal response, insufficient color density achieved by high speed recording, inconsistent color densities, time-course changes in the density of color image after recording, discoloration during preservation, degraded heat resistance of background, precipitation of white powder on a surface, which is what is called blooming, degraded re-printability and the like.

There has also been disclosed recently a method using a trisphenol compound as a developer or an antifading agent in JP-A-9-278695, JP-A-2001-96926 and the like, but the use of such compound does not lead to a sufficient color density. While JP-A-58-181686 discloses a method using 2,2'-methylenediphenol compound as a developer, the method described in this publication is insufficient in sensitivity and image stability, such as heat resistance, moisture resistance, weather resistance and the like.

It is also known to add a novolac resin to a color layer of a thermal recording material, but this is associated with a problem that sufficient sensitivity cannot be obtained.

As mentioned above, a thermal recording material having preservation stability as mentioned above, such as heat resistance and moisture resistance, which satisfies recent requirements for high sensitivity, has not been obtained yet.

In view of the above-mentioned situation, the present invention aims at providing a novel developer capable of realizing a thermal recording material superior in preservation stability (i.e., heat resistance, moisture resistance) of color image and non-image area, which satisfies recent requirements for high sensitivity, and a thermal recording material using the same.

DISCLOSURE OF THE INVENTION

As a result of intensive studies in an attempt to solve the above-mentioned problems, the present inventors have found that a composition containing a condensate having two cores of particular substituted phenols and formaldehyde as a main component, and condensate(s) having 3 or more cores (e.g., condensate having 3 cores, or condensate having 3 cores and condensate having 4 cores, or condensates having 3 to 5 cores) affords an extremely superior effect in improving the sensitivity of a thermal recording material, and in the preservation stability, which resulted in the completion of the present invention.

Accordingly, the present invention relates to (1) a developer for a thermal recording material comprising a composition comprising, of condensates represented by the formula (I):

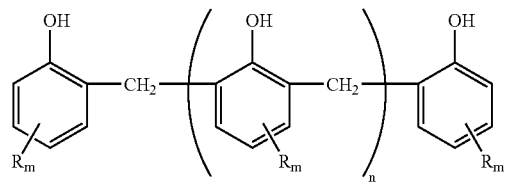

wherein

R is a halogen atom, a hydroxyl group, an alkyl group having 1 to 5 carbon atoms, an alkoxyl group having 1 to 5 carbon atoms, a cyano group, a nitro group, an aryl group or an aralkyl group, R in the number of m may be the same or different and m is an integer of 0–3, and n is an integer of 0–3, a condensate having two cores wherein $n=0$ as a main component, and at least one kind of condensate of the formula wherein $n=1-3$, (2) the developer for the thermal recording material of the above-mentioned (1), wherein the condensate having two cores wherein $n=0$ is contained in a proportion of 40–98%, (3) the developer for the thermal recording material of the above-mentioned (1) or (2), wherein the condensate has a halogen atom, a hydroxyl group, a lower alkyl group having 1 to 5 carbon atoms, an alkoxyl group having 1 to 5 carbon atoms, a cyano group, a nitro group, an aryl group or an aralkyl group at the p-position of a hydroxyl group of a phenol group, and (4) a thermal recording material comprising a support and a heat-coloring layer formed thereon, which layer comprises the developer of any of the above-mentioned (1)–(3) and a basic dye.

The present invention is explained in detail in the following.

In the aforementioned formula (I), n is an integer of 0–3. m is an integer of 0–3, preferably 1–3, more preferably 1. When m is 2 or 3, R in the number of m may be the same or different. When m is 1–3, R is preferably bonded to the m-position or p-position of hydroxyl group of phenol group, more preferably the p-position of hydroxyl group of phenol group.

The R in the number of m each shows halogen atom, hydroxyl group, alkyl group having 1 to 5 carbon atoms, alkoxyl group having 1 to 5 carbon atoms, cyano group, nitro group, aryl group or aralkyl group, preferably alkyl group having 1 to 5 carbon atoms or aralkyl group.

The halogen atom is exemplified by chlorine atom, bromine atom and fluorine atom, and is preferably chlorine atom. The alkyl group having 1 to 5 carbon atoms is exemplified by methyl, ethyl, propyl, isopropyl, t-butyl and t-amyl, preferably methyl, isopropyl and t-butyl. The alkoxyl group having 1 to 5 carbon atoms preferably has 1 to 4 carbon atoms. The alkoxyl group having 1 to 4 carbon atoms is exemplified by methoxy, ethoxy, propoxy, isopropoxy, butoxy and t-butoxy, and is preferably methoxy. The aryl group is exemplified by phenyl, tolyl and naphthyl, and is preferably phenyl. The aralkyl group is exemplified by cumyl and α-methylbenzyl.

The condensate having two cores, which is represented by the formula (I) (i.e., condensate of the formula wherein n=0), is concretely exemplified by
2,2'-methylenebisphenol,
2,2'-methylenebis(4-chlorophenol),
2,2'-methylenebis(5-chlorophenol),
2,2'-methylenebis(4-hydroxyphenol),
2,2'-methylenebis(5-hydroxyphenol),
2,2'-methylenebis(4-methylphenol),
2,2'-methylenebis(5-methylphenol),
2,2'-methylenebis(4-ethylphenol),
2,2'-methylenebis(5-ethylphenol),
2,2'-methylenebis(4-propylphenol),
2,2'-methylenebis(4-isopropylphenol),
2,2'-methylenebis(5-isopropylphenol),
2,2'-methylenebis(4-t-butylphenol),
2,2'-methylenebis(5-t-butylphenol),
2,2'-methylenebis(4-t-amylphenol),
2,2'-methylenebis(4-methoxyphenol),
2,2'-methylenebis(5-methoxyphenol),
2,2'-methylenebis(4-cyanophenol),
2,2'-methylenebis(5-cyanophenol),
2,2'-methylenebis(4-nitrophenol),
2,2'-methylenebis(5-nitrophenol),
2,2'-methylenebis(4-phenylphenol),
2,2'-methylenebis(5-phenylphenol),
2,2'-methylenebis(4-cumylphenol) and
2,2'-methylenebis[4-(α-methylbenzyl)phenol].

Of these, 2,2'-methylenebis(4-methylphenol), 2,2'-methylenebis(4-ethylphenol), 2,2'-methylenebis(4-isopropylphenol), 2,2'-methylenebis(4-t-butylphenol) and 2,2'-methylenebis(4-cumylphenol) are preferable, and 2,2'-methylenebis(4-t-butylphenol) and 2,2'-methylenebis(4-cumyl phenol) are particularly preferable.

Examples of the condensates having 3 to 5 cores, which are represented by the formula (I) (i.e., condensates of the formula wherein n=1–3), include compounds corresponding to the compounds exemplified for the aforementioned condensate having two cores.

The content of the condensate having two cores in the developer (composition) for thermal recording material of the present invention is preferably 40–98%, more preferably 40–90%, particularly preferably 50–85%, of the entire developer (composition). When the content of the condensate having two cores in the developer is less than 40%, or exceeds 98%, the objective effect of improving the sensitivity of a thermal recording material and preservation stability of color image and non-image area becomes difficult to express sufficiently. The developer for thermal recording material of the present invention can be produced by a known synthetic method comprising, for example, reacting substituted phenol represented by the formula (II):

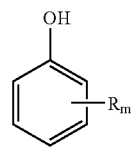

wherein R and m are as defined above, with formaldehyde in the presence of an acid catalyst (e.g., hydrochloric acid, p-toluenesulfonic acid and the like), and the like. The reaction is carried out in a suitable organic solvent inert to the reaction, which can dissolve the starting material and reaction product, such as water, methanol, ethanol, n-propyl alcohol, isopropyl alcohol, acetonitrile, toluene, chloroform, diethyl ether, N,N-dimethylacetamide, benzene, chlorobenzene, dichlorobenzene, diethyl ketone, ethyl methyl ketone, acetone, tetrahydrofuran and the like, at a reaction temperature of 0–150° C. for several hours to several dozen hours. The objective condensation composition thus obtained may contain a condensate of the formula (I) wherein n=not less than 4 as an impurity.

Specific examples of the substituted phenols represented by the formula (II) include phenol, p-chlorophenol, m-chlorophenol, o-chlorophenol, catechol, resorcinol, hydroquinone, p-cresol, m-cresol, o-cresol, p-ethylphenol, m-ethylphenol, o-ethylphenol, p-propylphenol, o-propylphenol, p-isopropylphenol, m-isopropylphenol, o-isopropylphenol, p-t-butylphenol, m-t-butylphenol, o-t-butylphenol, p-t-amylphenol, p-methoxyphenol, m-methoxyphenol, o-methoxyphenol, p-cyanophenol, m-cyanophenol, o-cyanophenol, p-nitrophenol, m-nitrophenol, o-nitrophenol, p-phenylphenol, m-phenylphenol, o-phenylphenol, p-cumylphenol, p-(α-methylbenzyl)phenol, o-(α-methylbenzyl)phenol and the like.

The thermal recording material (medium for thermal recording) of the present invention is constituted by forming a heat coloring layer containing the aforementioned developer of the present invention and a basic dye on a support.

In the thermal recording material of the present invention, the basic dye to be contained in the heat coloring layer may be any colorless to pale color basic dye known in the field of pressure sensitive or thermal recording paper and is not particularly limited. It is preferably a leucodye such as triphenylmethane, fluoran, fluorene, divinyl leucodyes and the like, particularly preferably fluoran leucodye, and most preferably anilinofluoran leucodye. The basic dye may be used alone or in combination of two or more kinds thereof.

Specific examples of the basic dye are shown in the following.

<Triphenylmethane Leucodye>
3,3-bis(p-dimethylaminophenyl)-6-dimethylaminophthalide
3,3-bis(p-dimethylaminophenyl)phthalide <Fluoran Leucodye>
3-diethylamino-6-methylfluoran
3-diethylamino-6-methyl-7-anilinofluoran
3-diethylamino-6-methyl-7-(o,p-dimethylanilino)fluoran
3-diethylamino-6-methyl-7-chlorofluoran
3-diethylamino-6-methyl-7-(m-trifluoromethylanilino)fluoran
3-diethylamino-6-methyl-7-(o-chloroanilino)fluoran
3-diethylamino-6-methyl-7-(p-chloroanilino)fluoran
3-diethylamino-6-methyl-7-(o-fluoroanilino)fluoran
3-diethylamino-6-methyl-7-(m-methylanilino)fluoran
3-diethylamino-6-chloro-7-methylfluoran
3-diethylamino-6-chloro-7-anilinofluoran
3-diethylamino-6-chloro-7-p-methylanilinofluoran
3-diethylamino-7-methylfluoran
3-diethylamino-7-chlorofluoran
3-diethylamino-7-(m-trifluoromethylanilino)fluoran
3-diethylamino-7-(o-chloroanilino)fluoran
3-diethylamino-7-(p-chloroanilino)fluoran
3-diethylamino-7-(o-fluoroanilino)fluoran
3-diethylamino-benzo[a]fluoran
3-diethylamino-benzo[c]fluoran
3-dibutylamino-6-methylfluoran
3-dibutylamino-6-methyl-7-anilinofluoran
3-dibutylamino-6-methyl-7-(o,p-dimethylanilino)fluoran
3-dibutylamino-6-methyl-7-(o-chloroanilino)fluoran
3-dibutylamino-6-methyl-7-(p-chloroanilino)fluoran
3-dibutylamino-6-methyl-7-(o-fluoroanilino)fluoran
3-dibutylamino-6-methyl-7-(m-trifluoromethylanilino)fluoran
3-dibutylamino-6-methyl-7-chlorofluoran
3-dibutylamino-6-chloro-7-anilinofluoran
3-dibutylamino-6-methyl-7-p-methylanilinofluoran
3-dibutylamino-7-(o-chloroanilino)fluoran
3-dibutylamino-7-(o-fluoroanilino)fluoran
3-di-n-pentylamino-6-methyl-7-anilinofluoran
3-di-n-pentylamino-6-methyl-7-(p-chloroanilino)fluoran
3-di-n-pentylamino-7-(m-trifluoromethylanilino)fluoran
3-di-n-pentylamino-6-chloro-7-anilinofluoran
3-di-n-pentylamino-7-(p-chloroanilino)fluoran
3-(N-ethyl-N-cyclohexylamino)-6-methyl-7-anilinofluoran
3-(N-ethyl-p-toluidino)-6-methyl-7-anilinofluoran
3-(N-ethyl-N-isoamylamino)-6-methyl-7-anilinofluoran
3-(N-ethyl-N-isoamylamino)-6-chloro-7-anilinofluoran
3-(N-ethyl-N-tetrahydrofrufurylamino)-6-methyl-7-anilinofluoran
3-(N-ethyl-N-isobutylamino)-6-methyl-7-anilinofluoran <Fluorene Leucodye>
3,6,6'-tris(dimethylamino)spiro[fluorene-9,3'-phthalide]
3,6,6'-tris(diethylamino)spiro[fluorene-9,3'-phthalide]

<Divinyl Leucodye>
3,3-bis[2-(p-dimethylaminophenyl)-2-(p-methoxyphenyl)ethenyl]-4,5,6,7-tetrabromophthalide
3,3-bis[2-(p-dimethylaminophenyl)-2-(p-methoxyphenyl)ethenyl]-4,5,6,7-tetrachlorophthalide
3,3-bis[1,1-bis(4-pyrrolidinophenyl)ethylen-2-yl]-4,5,6,7-tetrabromophthalide
3,3-bis[1-(4-methoxyphenyl)-1-(4-pyrrolidinophenyl)ethylen-2-yl]-4,5,6,7-tetrachlorophthalide <Other Basic Dyes>
3-(4-diethylamino-2-ethoxyphenyl)-3-(1-ethyl-2-methylindol-3-yl)-4-azaphthalide
3-(4-diethylamino-2-ethoxyphenyl)-3-(1-octyl-2-methylindol-3-yl)-4-azaphthalide
3-(4-cyclohexylethylamino-2-methoxyphenyl)-3-(1-ethyl-2-methylindol-3-yl)-4-azaphthalide
3,3-bis(1-ethyl-2-methylindol-3-yl)phthalide
3,6-bis(diethylamino)fluoran-γ-(3'-nitro)anilinolactam
3,6-bis(diethylamino)fluoran-γ-(4'-nitro)anilinolactam
1,1-bis[2',2',2",2"-tetrakis-(p-dimethylaminophenyl)ethenyl]-2,2-dinitrile ethane
1,1-bis[2',2',2",22"-tetrakis-(p-dimethylaminophenyl)ethenyl]-2-β-naphthoylethane
1,1-bis[2',2',22",2"-tetrakis-(p-dimethylaminophenyl)ethenyl]-2,2-diacetylethane
bis[2,2,2',2'-tetrakis-(p-dimethylaminophenyl)ethenyl]-methylmalonic acid dimethyl ester The heat coloring layer of the thermal recording material of the present invention may contain one or more conventionally known sensitizers to the extent that the effect of the present invention is not impaired. As such sensitizer, for example, stearic acid amide, palmitic acid amide, methoxycarbonyl-N-stearic acid benzamide, N-benzoylstearic acid amide, N-eicosanoic acid amide, ethylenebisstearic acid amide, behenic acid amide, methylenebisstearic acid amide, methylolamide, N-methylol stearic acid amide, dibenzyl terephthalate, diocthyl terephthalate, diocthyl terephthalate, benzyl p-benzyloxybenzoate, phenyl 1-hydroxy-2-naphthoate, dibenzyl oxalate, di-p-methylbenzyl oxalate, oxalic acid-di-p-chlorobenzyl, 2-naphthylbenzyl ether, p-benzyl biphenyl, 4-biphenyl-p-tolyl ether, di(p-methoxyphenoxyethyl) ether, 1,2-di(3-methylphenoxy)ethane, 1,2-di(4-methylphenoxy)ethane, 1,2-di(4-methoxyphenoxy)ethane, 1,2-di(4-chlorophenoxy)ethane, 1,2-diphenoxyethane, 1-(4-methoxyphenoxy)-2-(2-methylphenoxy)ethane, p-methylthiophenylbenzyl ether, 1,4-di(phenylthio)butane, p-acetotoluidide, p-acetophenetidide, N-acetoacetyl-p-toluidine, di(β-biphenylethoxy)benzene, p-di(vinyloxyethoxy)benzene, 1-isopropylphenyl-2-phenylethane, 1,2-bis(phenoxymethyl)benzene, p-toluenesulfonamide, o-toluenesulfonamide, di-p-tolyl carbonate, phenyl-α-naphthyl carbonate, diphenylsulfone and the like can be mentioned. Particularly, benzyl p-benzyloxybenzoate, stearic acid amide, ethylenebisstearic acid amide, di-p-methylbenzyl oxalate, oxalic di-p-chlorobenzyl oxalate, 2-naphthylbenzyl ether, p-benzylbiphenyl, 4-biphenyl-p-tolyl ether, 1,2-di(3-methylphenoxy)ethane, 1,2-bis(phenoxymethyl)benzene and diphenylsulfone are preferable, and of these, when stearic acid amide, ethylenebisstearic acid amide, oxalic acid-di-p-methylbenzyl, di-p-chlorobenzyl oxalate, 2-naphthylbenzyl ether, p-benzyl biphenyl, 1,2-di(3-methylphenoxy)ethane, 1,2-bis(phenoxymethyl)benzene and the like are used in combination with a condensation composition containing 2,2'-methylenebis(4-t-butylphenol) as a main component from among the developers of the present invention, more preferable results can be obtained.

The heat coloring layer may contain a conventionally known organic developer to the extent that the effect of the present invention is not inhibited. Examples of such conventionally known developer include 4-hydroxybenzoic acid esters, 4-hydroxyphthalic acid diesters, phthalic acid monoesters, bis(hydroxyphenyl)sulfides, 4-hydroxyphenylarylsulfones (e.g., 4-(4-propoxy-benzenesulfonyl)phenol, 4-(4-isopropoxy-benzenesulfonyl)phenol and the like), 4-hydroxyphenylarylsulfonates, 1,3-di[2-(hydroxyphenyl)-2-propyl]benzenes, 4-hydroxybenzoyloxybenzoic acid esters, bisphenolsulfones and the like.

The production method of the thermal recording material of the present invention is not particularly limited, but generally, the developer of the present invention, a basic dye, and an additive such as a sensitizer and the like, which is added as necessary, are dispersed in a solution of a binder or an emulsion of a binder or a dispersion containing a binder in paste therein to give a coating liquid, and the liquid is applied to a support and dried to form a heat coloring layer.

Examples of the above-mentioned binder include completely saponified polyvinyl alcohol having a polymerization degree of 200–1900, partially saponified polyvinyl alcohol, carboxy denatured polyvinyl alcohol, amide denatured polyvinyl alcohol, sulfonic acid denatured polyvinyl alcohol, butyral denatured polyvinyl alcohol, other denatured polyvinyl alcohols, hydroxyethyl cellulose, methyl cellulose, carboxymethyl cellulose, styrene-maleic anhydride copolymer, styrene-butadiene copolymer and cellulose derivatives such as ethyl cellulose and acetyl cellulose, polyvinyl chloride, polyvinyl acetate, polyacrylamide, polyacrylic acid ester, polyvinylbutyral polystyrol and copolymers thereof, polyamide resin, silicone resin, petroleum resin, terpene resin, ketone resin, cumarone resin and the like. These polymers can be used alone or in combination of two or more kinds thereof according to the requested quality. They may be dissolved in a solvent such as water, alcohol, ketone, ester, hydrocarbon and the like, or emulsified or dispersed in paste in water or other medium and used.

In the present invention, the filler to be added to a heat coloring layer is exemplified by inorganic or organic fillers such as silica, calcium carbonate, kaolin, calcined kaolin, diatomaceous earth, talc, titanium oxide, zinc oxide, aluminum hydroxide, polystyrene resin, urea-formalin resin, styrene-methacrylic acid copolymer, styrene-butadiene copolymer, hollow plastic pigment and the like, and the like.

Other than these, stabilizers such as p-nitrobenzoic acid metal salt (Ca, Zn), phthalic acid monobenzyl ester metal salt (Ca, Zn) and the like, releasing agents such as fatty acid metal salt and the like, lubricants such as wax and the like, benzophenone or triazole ultraviolet absorbents, water resistant additives such as glyoxal and the like, dispersing agents, antifoaming agents and the like can be added as necessary.

In the present invention, the kind and amount of use of each material such as basic dye, developer, sensitizer, binder, loading material and the like to be used for the heat coloring layer are determined as appropriate depending on various performances that a heat coloring layer is requested to show, and are not particularly limited. In a most general example, about 1–8 parts by weight of a developer and 1–20 parts by weight of a filler, when it is to be added, are added suitably per 1 part by weight of a basic dye. When a sensitizer is to be added, the sensitizer is added suitably in an amount of 0.1–2 parts by weight per 1 part by weight of a developer, and a binder is added suitably in an amount of about 10–25 wt % of the entire solid content.

When a thermal recording material is to be produced according to this method, the basic dye and the developer, and the additives to be added where necessary are preferably used after atomization in a grinding machine such as a ball mill, an attriter, a sand grinder and the like or in a suitable emulsification apparatus to a particle size of not more than several microns before use.

As a support on which to form a heat coloring layer, paper, recycled paper, synthetic paper, plastic film, foamed plastic film, nonwoven fabric, metal foil and the like can be used, and a composite sheet combining these can be also used.

In the thermal recording material of the present invention, moreover, preservability can be enhanced by forming an overcoating layer made of a polymer containing an organic loading material, and the like on the heat coloring layer. Moreover, preservability and sensitivity can be enhanced by forming an undercoating layer containing an organic and/or an inorganic loading material under the heat coloring layer.

EXAMPLES

The present invention is explained in detail by referring to Examples, which are not to be construed as limitative. In the explanation, "part" means "part by weight".

The composition ratio of the 2,2'-methylenebis(4-methylphenol) 80% condensation composition product described below is as follows.
2,2'-methylenebis(4-methylphenol):2,6-bis(2-hydroxy-5-methylbenzyl)-4-methylphenol:2,2'-methylenebis[6-[(2-hydroxy-5-methylphenyl)methyl]-4-methylphenol]=81:18:1

The composition ratio of the 2,2'-methylenebis(4-isopropylphenol) 60% condensation composition product is as follows.
2,2'-methylenebis(4-isopropylphenol):2,6-bis(2-hydroxy-5-isopropylbenzyl)-4-isopropylphenol:2,2'-methylenebis[6-[(2-hydroxy-5-isopropylphenyl)methyl]-4-isopropylphenol]=59:37:4

The composition ratio of the 2,2'-methylenebis(4-t-butylphenol) 40% condensation composition product is as follows.
2,2'-methylenebis(4-t-butylphenol):2,6-bis(2-hydroxy-5-t-butylbenzyl)-4-t-butylphenol:2,2'-methylenebis[6-(2-hydroxy-5-t-butylphenyl)methyl]-4-t-butylphenol:2,6-bis[[2-hydroxy-3-[(2-hydroxy-5-t-butylphenyl)methyl]-5-t-butylphenyl]methyl]-4-t-butylphenol=40:32:19:9

The composition ratio of the 2,2'-methylenebis(4-t-butylphenol) 55% condensation composition product is as follows.
2,2'-methylenebis(4-t-butylphenol):2,6-bis(2-hydroxy-5-t-butylbenzyl)-4-t-butylphenol:2,2'-methylenebis[6-[(2-hydroxy-5-t-butylphenyl)methyl]-4-t-butylphenol]:2,6-bis[[2-hydroxy-3-[(2-hydroxy-5-t-butylphenyl)methyl]-5-t-butylphenyl]methyl]-4-t-butylphenol=55:32:10:3

The composition ratio of the 2,2'-methylenebis(4-t-butylphenol) 70% condensation composition product is as follows.
2,2'-methylenebis(4-t-butylphenol):2,6-bis(2-hydroxy-5-t-butylbenzyl)-4-t-butylphenol:2,2'-methylenebis[6-[(2-hydroxy-5-t-butylphenyl)methyl]-4-t-butylphenol]=72:27:1

The composition ratio of the 2,2'-methylenebis(4-t-butylphenol) 80% condensation composition product is as follows.
2,2'-methylenebis(4-t-butylphenol):2,6-bis(2-hydroxy-5-t-butylbenzyl)-4-t-butylphenol:2,2'-methylenebis[6-[(2-hydroxy-5-t-butylphenyl)methyl]-4-t-butylphenol]=79:18:3

The composition ratio of the 2,2'-methylenebis(4-t-butylphenol) 90% condensation composition product is as follows.
2,2'-methylenebis(4-t-butylphenol):2,6-bis(2-hydroxy-5-t-butylbenzyl)-4-t-butylphenol=92:8

The composition ratio of the 2,2'-methylenebis(4-cumylphenol) 60% condensation composition product is as follows.
2,2'-methylenebis(4-cumylphenol):2,6-bis(2-hydroxy-5-cumylbenzyl)-4-cumylphenol:2,2'-methylenebis[(2-hydroxy-5-cumylphenyl)methyl]-4-cumylphenol:2,6-bis[[2-hydroxy-3-[(2-hydroxy-5-cumylphenyl)methyl]-5-cumylphenyl]methyl]-4-cumylphenol=60:26:10:4

Example 1

| Liquid A (developer dispersion) | |
| --- | --- |
| condensation composition containing 80% of 2,2'-methylenebis(4-methylphenol) | 6.0 parts |
| 10% aqueous polyvinyl alcohol solution | 18.8 parts |
| water | 11.2 parts |
| Liquid B (sensitizer dispersion) | |
| diphenylsulfone | 4.0 parts |
| 10% aqueous polyvinyl alcohol solution | 12.5 parts |
| water | 7.5 parts |
| Liquid C (dye dispersion) | |
| 3-(N-ethyl-N-isoamylamino)-6-methyl-7-anilinofluoran | 2.0 parts |
| 10% aqueous polyvinyl alcohol solution | 4.6 parts |
| water | 2.6 parts |

The above-mentioned Liquid A, Liquid B and Liquid C were ground in a sand grinder to an average particle size of 1 micron. The dispersions were mixed at the following ratio to give a coating liquid.

| Liquid A (developer dispersion) | 36.0 parts |
| --- | --- |
| Liquid B (sensitizer dispersion) | 24.0 parts |
| Liquid C (dye dispersion) | 9.2 parts |
| Kaolin clay (50% dispersion) | 12.0 parts |

The above-mentioned coating liquid was applied to one side of a basic paper having a basic weight of 50 g/m² in a coating amount of 6.0 g/m² and dried at room temperature for 24 hr. This sheet was treated with a supercalender to smoothness of 500–600 sec to give a thermal recording material. The coated amount here means the amount of the solid adhered to the support after drying.

Example 2

In the same manner as in Example 1 except that a condensation composition containing 60% of 2,2'-methylenebis(4-isopropylphenol) was used instead of the condensation composition containing 80% of 2,2'-methylenebis(4-methylphenol) used for Liquid A (developer dispersion) and diphenylsulfone of Liquid B (sensitizer dispersion) was not used, a thermal recording material was prepared.

Example 3

In the same manner as in Example 1 except that a condensation composition containing 60% of 2,2'-methylenebis(4-isopropylphenol) was used instead of the condensation composition containing 80% of 2,2'-methylenebis(4-methylphenol) used for Liquid A (developer dispersion), a thermal recording material was prepared.

Example 4

In the same manner as in Example 1 except that a condensation composition containing 60% of 2,2'-methylenebis(4-isopropylphenol) was used instead of the condensation composition containing 80% of 2,2'-methylenebis(4-methylphenol) used for Liquid A (developer dispersion), and 4-biphenyl-p-tolyl ether was used instead of diphenylsulfone used for Liquid B (sensitizer dispersion), a thermal recording material was prepared.

Example 5

In the same manner as in Example 1 except that a condensation composition containing 40% of 2,2'-methylenebis(4-t-butylphenol) was used instead of the condensation composition containing 80% of 2,2'-methylenebis(4-methylphenol) used for Liquid A (developer dispersion) and diphenylsulfone of Liquid B (sensitizer dispersion) was not used, a thermal recording material was prepared.

Example 6

In the same manner as in Example 1 except that a condensation composition containing 40% of 2,2'-methylenebis(4-t-butylphenol) was used instead of the condensation composition containing 80% of 2,2'-methylenebis(4-methylphenol) used for Liquid A (developer dispersion), a thermal recording material was prepared.

Example 7

In the same manner as in Example 1 except that a condensation composition containing 40% of 2,2'-methylenebis(4-t-butylphenol) was used instead of the condensation composition containing 80% of 2,2'-methylenebis(4-methylphenol) used for Liquid A (developer dispersion) and 4-biphenyl-p-tolyl ether was used instead of diphenylsulfone used for Liquid B (sensitizer dispersion), a thermal recording material was prepared.

Example 8

In the same manner as in Example 1 except that a condensation composition containing 55% of 2,2'-methylenebis(4-t-butylphenol) was used instead of the condensation composition containing 80% of 2,2'-methylenebis(4-methylphenol) used for Liquid A (developer dispersion) and diphenylsulfone of Liquid B (sensitizer dispersion) was not used, a thermal recording material was prepared.

Example 9

In the same manner as in Example 1 except that a condensation composition containing 55% of 2,2'-methylenebis(4-t-butylphenol) was used instead of the condensation composition containing 80% of 2,2'-methylenebis(4-methylphenol) used for Liquid A (developer dispersion), a thermal recording material was prepared.

Example 10

In the same manner as in Example 1 except that a condensation composition containing 55% of 2,2'-methylenebis(4-t-butylphenol) was used instead of the condensation composition containing 80% of 2,2'-methylenebis(4-methylphenol) used for Liquid A (developer dispersion) and 4-biphenyl-p-tolyl ether was used instead of diphenylsulfone used for Liquid B (sensitizer dispersion), a thermal recording material was prepared.

Example 11

In the same manner as in Example 1 except that a condensation composition containing 70% of 2,2'-methylenebis(4-t-butylphenol) was used instead of the condensation composition containing 80% of 2,2'-methylenebis(4-methylphenol) used for Liquid A (developer dispersion) and diphenylsulfone of Liquid B (sensitizer dispersion) was not used, a thermal recording material was prepared.

Example 12

In the same manner as in Example 1 except that a condensation composition containing 70% of 2,2'-methylenebis(4-t-butylphenol) was used instead of the condensation composition containing 80% of 2,2'-methylenebis(4-methylphenol) used for Liquid A (developer dispersion), a thermal recording material was prepared.

Example 13

In the same manner as in Example 1 except that a condensation composition containing 70% of 2,2'-methylenebis(4-t-butylphenol) was used instead of the condensation composition containing 80% of 2,2'-methylenebis(4-methylphenol) used for Liquid A (developer dispersion) and 4-biphenyl-p-tolyl ether was used instead of diphenylsulfone used for Liquid B (sensitizer dispersion), a thermal recording material was prepared.

Example 14

In the same manner as in Example 1 except that a condensation composition containing 80% of 2,2'-methylenebis(4-t-butylphenol) was used instead of the condensation composition containing 80% of 2,2'-methylenebis(4-methylphenol) used for Liquid A (developer dispersion) and diphenylsulfone of Liquid B (sensitizer dispersion) was not used, a thermal recording material was prepared.

Example 15

In the same manner as in Example 1 except that a condensation composition containing 80% of 2,2'-methylenebis(4-t-butylphenol) was used instead of the condensation composition containing 80% of 2,2'-methylenebis(4-methylphenol) used for Liquid A (developer dispersion), a thermal recording material was prepared.

Example 16

In the same manner as in Example 1 except that a condensation composition containing 80% of 2,2'-methylenebis(4-t-butylphenol) was used instead of the condensation composition containing 80% of 2,2'-methylenebis(4-methylphenol) used for Liquid A (developer dispersion) and 4-biphenyl-p-tolyl ether was used instead of diphenylsulfone used for Liquid B (sensitizer dispersion), a thermal recording material was prepared.

Example 17

In the same manner as in Example 1 except that a condensation composition containing 90% of 2,2'-methylenebis(4-t-butylphenol) was used instead of the condensation composition containing 80% of 2,2'-methylenebis(4-methylphenol) used for Liquid A (developer dispersion) and diphenylsulfone of Liquid B (sensitizer dispersion) was not used, a thermal recording material was prepared.

Example 18

In the same manner as in Example 1 except that a condensation composition containing 90% of 2,2'-methylenebis(4-t-butylphenol) was used instead of the condensation composition containing 80% of 2,2'-methylenebis(4-methylphenol) used for Liquid A (developer dispersion), a thermal recording material was prepared.

Example 19

In the same manner as in Example 1 except that a condensation composition containing 90% of 2,2'-methylenebis(4-t-butylphenol) was used instead of the condensation composition containing 80% of 2,2'-methylenebis(4-methylphenol) used for Liquid A (developer dispersion) and 4-biphenyl-p-tolyl ether was used instead of diphenylsulfone used for Liquid B (sensitizer dispersion), a thermal recording material was prepared.

Example 20

In the same manner as in Example 1 except that a condensation composition containing 60% of 2,2'-methylenebis(4-cumylphenol) was used instead of the condensation composition containing 80% of 2,2'-methylenebis(4-methylphenol) used for Liquid A (developer dispersion) and diphenylsulfone of Liquid B (sensitizer dispersion) was not used, a thermal recording material was prepared.

Example 21

In the same manner as in Example 1 except that a condensation composition containing 60% of 2,2'-methylenebis(4-cumylphenol) was used instead of the condensation composition containing 80% of 2,2'-methylenebis(4-methylphenol) used for Liquid A (developer dispersion), a thermal recording material was prepared.

Example 22

In the same manner as in Example 1 except that a condensation composition containing 60% of 2,2'-methylenebis(4-cumylphenol) was used instead of the condensation composition containing 80% of 2,2'-methylenebis(4-methylphenol) used for Liquid A (developer dispersion) and 4-biphenyl-p-tolyl ether was used instead of diphenylsulfone used for Liquid B (sensitizer dispersion), a thermal recording material was prepared.

Example 23

In the same manner as in Example 1 except that a condensation composition containing 90% of 2,2'-methylenebis(4-t-butylphenol) was used instead of the condensation composition containing 80% of 2,2'-methylenebis(4-methylphenol) used for Liquid A (developer dispersion) and stearic acid amide was used instead of diphenylsulfone used for Liquid B (sensitizer dispersion), a thermal recording material was prepared.

Example 24

In the same manner as in Example 1 except that a condensation composition containing 90% of 2,2'-methylenebis(4-t-butylphenol) was used instead of the condensation composition containing 80% of 2,2'-methylenebis(4-methylphenol) used for Liquid A (developer dispersion) and ethylenebisstearic acid amide was used instead of diphenylsulfone used for Liquid B (sensitizer dispersion), a thermal recording material was prepared.

Example 25

In the same manner as in Example 1 except that a condensation composition containing 90% of 2,2'-methylenebis(4-t-butylphenol) was used instead of the condensation composition containing 80% of 2,2'-methylenebis(4-methylphenol) used for Liquid A (developer dispersion) and 2-naphthylbenzyl ether was used instead of diphenylsulfone used for Liquid B (sensitizer dispersion), a thermal recording material was prepared.

Example 26

In the same manner as in Example 1 except that a condensation composition containing 90% of 2,2'-methylenebis(4-t-butylphenol) was used instead of the condensation composition containing 80% of 2,2'-methylenebis(4-methylphenol) used for Liquid A (developer dispersion) and di-p-methylbenzyl oxalate was used instead of diphenylsulfone used for Liquid B (sensitizer dispersion), a thermal recording material was prepared.

Example 27

In the same manner as in Example 1 except that a condensation composition containing 90% of 2,2'-methylenebis(4-t-butylphenol) was used instead of the condensation composition containing 80% of 2,2'-methylenebis(4-methylphenol) used for Liquid A (developer dispersion) and di-p-chlorobenzyl oxalate was used instead of diphenylsulfone used for Liquid B (sensitizer dispersion), a thermal recording material was prepared.

Example 28

In the same manner as in Example 1 except that a condensation composition containing 90% of 2,2'-methylenebis(4-t-butylphenol) was used instead of the condensation composition containing 80% of 2,2'-methylenebis(4-methylphenol) used for Liquid A (developer dispersion) and p-benzyl biphenyl was used instead of diphenylsulfone used for Liquid B (sensitizer dispersion), a thermal recording material was prepared.

Example 29

In the same manner as in Example 1 except that a condensation composition containing 90% of 2,2'-methylenebis(4-t-butylphenol) was used instead of the condensation composition containing 80% of 2,2'-methylenebis(4-methylphenol) used for Liquid A (developer dispersion) and 1,2-di(3-methylphenoxy)ethane was used instead of diphenylsulfone used for Liquid B (sensitizer dispersion), a thermal recording material was prepared.

Example 30

In the same manner as in Example 1 except that a condensation composition containing 90% of 2,2'-methylenebis(4-t-butylphenol) was used instead of the condensation composition containing 80% of 2,2'-methylenebis(4-methylphenol) used for Liquid A (developer dispersion) and 1,2-diphenoxyethane was used instead of diphenylsulfone used for Liquid B (sensitizer dispersion), a thermal recording material was prepared.

Example 31

In the same manner as in Example 1 except that a condensation composition containing 90% of 2,2'-methylenebis(4-t-butylphenol) was used instead of the condensation composition containing 80% of 2,2'-methylenebis(4-methylphenol) used for Liquid A (developer dispersion) and 1,2-bis(phenoxymethyl)benzene was used instead of diphenylsulfone used for Liquid B (sensitizer dispersion), a thermal recording material was prepared.

Example 32

In the same manner as in Example 1 except that a condensation composition containing 55% of 2,2'-methylenebis(4-t-butylphenol) was used instead of the condensation composition containing 80% of 2,2'-methylenebis(4-methylphenol) used for Liquid A (developer dispersion), 1,2-di(3-methylphenoxy)ethane was used instead of diphenylsulfone used for Liquid B (sensitizer dispersion) and 3-di-n-pentylamino-6-methyl-7-anilinofluoran was used instead of 3-(N-ethyl-N-isoamylamino)-6-methyl-7-anilinofluoran used for Liquid C (dye dispersion), a thermal recording material was prepared.

Example 33

In the same manner as in Example 1 except that a condensation composition containing 55% of 2,2'-methylenebis(4-t-butylphenol) was used instead of the condensation composition containing 80% of 2,2'-methylenebis(4-methylphenol) used for Liquid A (developer dispersion), di-p-methylbenzyl oxalate was used instead of diphenylsulfone used for Liquid B (sensitizer dispersion) and 3-di-n-butylamino-6-methyl-7-anilinofluoran was used instead of 3-(N-ethyl-N-isoamylamino)-6-methyl-7-anilinofluoran used for Liquid C (dye dispersion), a thermal recording material was prepared.

Example 34

In the same manner as in Example 1 except that a condensation composition containing 55% of 2,2'-methylenebis(4-t-butylphenol) was used instead of the condensation composition containing 80% of 2,2'-methylenebis(4-methylphenol) used for Liquid A (developer dispersion), 1,2-bis(phenoxymethyl)benzene was used instead of diphenylsulfone used for Liquid B (sensitizer dispersion) and 3-di-n-pentylamino-6-methyl-7-anilinofluoran was used instead of 3-(N-ethyl-N-isoamylamino)-6-methyl-7-anilinofluoran used for Liquid C (dye dispersion), a thermal recording material was prepared.

Example 35

In the same manner as in Example 1 except that a condensation composition containing 55% of 2,2'-methylenebis(4-t-butylphenol) was used instead of the condensation composition containing 80% of 2,2'-methylenebis(4-methylphenol) used for Liquid A (developer dispersion), 1,2-bis(phenoxymethyl)benzene was used instead of diphenylsulfone used for Liquid B (sensitizer dispersion) and 3-di-n-butylamino-6-methyl-7-anilinofluoran was used instead of 3-(N-ethyl-N-isoamylamino)-6-methyl-7-anilinofluoran used for Liquid C (dye dispersion), a thermal recording material was prepared.

Example 36

In the same manner as in Example 1 except that a condensation composition containing 55% of 2,2'-methylenebis(4-t-butylphenol) was used instead of the condensation composition containing 80% of 2,2'-methylenebis(4-methylphenol) used for Liquid A (developer dispersion), 1,2-bis(phenoxymethyl)benzene was used instead of diphenylsulfone used for Liquid B (sensitizer dispersion) and a mixture of 3-di-n-pentylamino-6-methyl-7-anilinofluoran (50 wt %) and 3-di-n-butylamino-6-methyl-7-anilinofluoran (50 wt %) was used instead of 3-(N-ethyl-N-isoamylamino)-6-methyl-7-anilinofluoran used for Liquid C (dye dispersion), a thermal recording material was prepared.

Example 37

In the same manner as in Example 1 except that a condensation composition containing 55% of 2,2'-methylenebis(4-t-butylphenol) was used-instead of the condensation composition containing 80% of 2,2'-methylenebis(4-methylphenol) used for Liquid A (developer dispersion), 1,2-di(3-methylphenoxy)ethane was used instead of diphenylsulfone used for Liquid B (sensitizer dispersion) and a mixture of 3-di-n-butylamino-6-methyl-7-anilinofluoran (50 wt %) and 3-(N-ethyl-N-isoamylamino)-6-methyl-7-anilinofluoran (50 wt %) was used instead of 3-(N-ethyl-N-isoamylamino)-6-methyl-7-anilinofluoran used for Liquid C (dye dispersion), a thermal recording material was prepared.

Example 38

In the same manner as in Example 1 except that a condensation composition containing 55% of 2,2'-methylenebis(4-t-butylphenol) was used instead of the condensation composition containing 80% of 2,2'-methylenebis(4-methylphenol) used for Liquid A (developer dispersion), di-p-methylbenzyl oxalate was used instead of diphenylsulfone used for Liquid B (sensitizer dispersion) and a mixture of 3-di-n-pentylamino-6-methyl-7-anilinofluoran (50 wt %) and 3-(N-ethyl-N-isoamylamino)-6-methyl-7-anilinofluoran (50 wt %) was used instead of 3-(N-ethyl-N-isoamylamino)-6-methyl-7-anilinofluoran used for Liquid C (dye dispersion), a thermal recording material was prepared.

Comparative Example 1

In the same manner as in Example 1 except that 2,2'-methylenebis(4-isopurpylphenol) was used instead of the condensation composition containing 80% of 2,2'-methylenebis(4-methylphenol) used for Liquid A (developer dispersion) and diphenylsulfone of Liquid B (sensitizer dispersion) was not used, a thermal recording material was prepared.

Comparative Example 2

In the same manner as in Example 1 except that 2,2'-methylenebis(4-t-butylphenol) instead of a condensation composition containing 80% of 2,2'-methylenebis(4-methyl phenol) used for Liquid A (developer dispersion) in Example 1 and diphenylsulfone of Liquid B (sensitizer dispersion) was not used, a thermal recording material was prepared.

Comparative Example 3

In the same manner as in Example 1 except that phenol novolac resin (Phenolite TD2090) manufactured by DAINIPPON INK AND CHEMICALS, INCORPORATED was used instead of the condensation composition containing 80% of 2,2'-methylenebis(4-methylphenol) used for Liquid A (developer dispersion) and diphenylsulfone of Liquid B (sensitizer dispersion) was not used, a thermal recording material was prepared.

Comparative Example 4

In the same manner as in Example 1 except that phenol novolac resin (Phenolite TD2090) manufactured by DAINIPPON INK AND CHEMICALS, INCORPORATED was used instead of the condensation composition containing 80% of 2,2'-methylenebis(4-methylphenol) used for Liquid A (developer dispersion), a thermal recording material was prepared.

The thermal recording materials obtained in the above Examples and Comparative Examples were tested for the following quality and performance. The results are shown in Tables 1–6. In the Tables, the numerals in the upper line show the density of the recorded area and those in the lower line show the density of the non-image area.

(1) Thermal Recordability Test (Dynamic Color Density)

The prepared thermal recording materials were subjected to printing using TH-PMD manufactured by Ohkura Electric Co., Ltd. (thermal printer, equipped with a thermal head manufactured by Kyocera Corporation) at an impression energy of 0.38 mj/dot. The image density of the recorded area was measured with the Macbeth densitometer (RD-914, using Amber Filter).

(2) Preservation Stability Test

[Heat Resistance Test]

The thermal recording materials printed on in the thermal recordability test were stood for 24 hr in a high temperature dry environment at a test temperature of 60° C., and the image densities of the recorded area and the non-image area were measured with the Macbeth densitometer.

[Moisture Resistance Test]

The thermal recording materials printed on in the thermal recordability test were stood for 24 hr in an environment of a test temperature 40° C. and 90% RH, and the image densities of the recorded area and the non-image area were measured with the Macbeth densitometer.

TABLE 1

| | developer | sensitizer | | dynamic color density | heat resistance | moisture resistance |
|---|---|---|---|---|---|---|
| Ex. 1 | condensation composition containing 80% of 2,2'-methylenebis-(4-methylphenol) | diphenyl-sulfone | recorded area | 1.35 | 1.00 | 1.15 |
| | | | non-image area | 0.09 | 0.10 | 0.10 |
| Ex. 2 | condensation composition containing 60% of 2,2'-methylenebis-(4-isopropylphenol) | none | recorded area | 1.18 | 0.99 | 1.01 |
| | | | non-image area | 0.08 | 0.10 | 0.09 |
| Ex. 3 | condensation composition containing 60% of 2,2'-methylenebis-(4-isopropylphenol) | diphenyl-sulfone | recorded area | 1.36 | 0.83 | 0.94 |
| | | | non-image area | 0.04 | 0.09 | 0.07 |
| Ex. 4 | condensation composition containing 60% of 2,2'-methylenebis-(4-isopropylphenol) | 4-biphenyl-p-tolyl ether | recorded area | 1.40 | 0.80 | 1.02 |
| | | | non-image area | 0.05 | 0.10 | 0.05 |
| Ex. 5 | condensation composition containing 40% of 2,2'-methylenebis-(4-t-butylphenol) | none | recorded area | 1.00 | 0.95 | 0.98 |
| | | | non-image area | 0.05 | 0.08 | 0.07 |
| Ex. 6 | condensation composition containing 40% of 2,2'-methylenebis-(4-t-butylphenol) | diphenyl-sulfone | recorded area | 1.11 | 1.02 | 1.16 |
| | | | non-image area | 0.05 | 0.11 | 0.06 |
| Ex. 7 | condensation composition containing 40% of 2,2'-methylenebis-(4-t-butylphenol) | 4-biphenyl-p-tolyl ether | recorded area | 1.23 | 1.01 | 1.01 |
| | | | non-image area | 0.04 | 0.08 | 0.04 |
| Ex. 8 | condensation composition containing 55% of 2,2'-methylenebis-(4-t-butylphenol) | none | recorded area | 1.01 | 0.93 | 0.98 |
| | | | non-image area | 0.06 | 0.08 | 0.09 |
| Ex. 9 | condensation composition containing 55% of 2,2'-methylenebis-(4-t-butylphenol) | diphenyl-sulfone | recorded area | 1.21 | 1.10 | 1.21 |
| | | | non-image area | 0.06 | 0.08 | 0.07 |
| Ex. 10 | condensation composition containing 55% of 2,2'-methylenebis-(4-t-butylphenol) | 4-biphenyl-p-tolyl ether | recorded area | 1.36 | 1.12 | 1.24 |
| | | | non-image area | 0.06 | 0.08 | 0.06 |
| Ex. 11 | condensation composition containing 70% of 2,2'-methylenebis-(4-t-butylphenol) | none | recorded area | 1.20 | 1.00 | 1.10 |
| | | | non-image area | 0.09 | 0.11 | 0.11 |

TABLE 2

| | developer | sensitizer | | dynamic color density | heat resistance | moisture resistance |
|---|---|---|---|---|---|---|
| Ex. 12 | condensation composition containing 70% of 2,2'-methylenebis-(4-t-butylphenol) | diphenyl-sulfone | recorded area | 1.31 | 1.07 | 1.11 |
| | | | non-image area | 0.04 | 0.06 | 0.04 |
| Ex. 13 | condensation composition containing 70% of 2,2'-methylenebis-(4-t-butylphenol) | 4-biphenyl-p-tolyl ether | recorded area | 1.33 | 1.02 | 1.03 |
| | | | non-image area | 0.05 | 0.05 | 0.04 |

TABLE 2-continued

| | developer | sensitizer | | dynamic color density | heat resistance | moisture resistance |
|---|---|---|---|---|---|---|
| Ex. 14 | condensation composition containing 80% of 2,2'-methylenebis-(4-t-butylphenol) | none | recorded area | 1.15 | 0.99 | 1.00 |
| | | | non-image area | 0.08 | 0.09 | 0.08 |
| Ex. 15 | condensation composition containing 80% of 2,2'-methylenebis-(4-t-butylphenol) | diphenyl-sulfone | recorded area | 1.36 | 1.04 | 1.27 |
| | | | non-image area | 0.10 | 0.11 | 0.10 |
| Ex. 16 | condensation composition containing 80% of 2,2'-methylenebis-(4-t-butylphenol) | 4-biphenyl-p-tolyl ether | recorded area | 1.36 | 0.95 | 1.25 |
| | | | non-image area | 0.10 | 0.10 | 0.10 |
| Ex. 17 | condensation composition containing 90% of 2,2'-methylenebis-(4-t-butylphenol) | none | recorded area | 1.10 | 0.97 | 1.01 |
| | | | non-image area | 0.09 | 0.11 | 0.11 |
| Ex. 18 | condensation composition containing 90% of 2,2'-methylenebis-(4-t-butylphenol) | diphenyl-sulfone | recorded area | 1.36 | 0.81 | 1.10 |
| | | | non-image area | 0.08 | 0.09 | 0.09 |
| Ex. 19 | condensation composition containing 90% of 2,2'-methylenebis-(4-t-butylphenol) | 4-biphenyl-p-tolyl ether | recorded area | 1.39 | 0.80 | 1.10 |
| | | | non-image area | 0.08 | 0.10 | 0.09 |
| Ex. 20 | condensation composition containing 60% of 2,2'-methylenebis-(4-cumylphenol) | none | recorded area | 1.00 | 0.98 | 0.95 |
| | | | non-image area | 0.06 | 0.07 | 0.06 |
| Ex. 21 | condensation composition containing 60% of 2,2'-methylenebis-(4-cumylphenol) | diphenyl-sulfone | recorded area | 1.13 | 1.07 | 1.13 |
| | | | non-image area | 0.08 | 0.09 | 0.10 |
| Ex. 22 | condensation composition containing 60% of 2,2'-methylenebis-(4-cumylphenol) | 4-biphenyl p-tolyl ether | recorded area | 1.28 | 1.13 | 1.27 |
| | | | non-image area | 0.07 | 0.10 | 0.11 |

TABLE 3

| | developer | sensitizer | | dynamic color density | heat resistance | moisture resistance |
|---|---|---|---|---|---|---|
| Ex. 23 | condensation composition containing 90% of 2,2'-methylenebis-(4-t-butylphenol) | stearic acid amide | recorded area | 1.36 | 0.98 | 1.17 |
| | | | non-image area | 0.08 | 0.08 | 0.10 |
| Ex. 24 | condensation composition containing 90% of 2,2'-methylenebis-(4-t-butylphenol) | ethylene bis-stearic acid amide | recorded area | 1.32 | 1.02 | 1.13 |
| | | | non-image area | 0.08 | 0.09 | 0.09 |
| Ex. 25 | condensation composition containing 90% of 2,2'-methylenebis-(4-t-butylphenol) | 2-naphthyl benzyl-ether | recorded area | 1.37 | 1.07 | 1.15 |
| | | | non-image area | 0.07 | 0.09 | 0.10 |
| Ex. 26 | condensation composition containing 90% of 2,2'-methylenebis-(4-t-butylphenol) | di-p-methyl-benzyl oxalate | recorded area | 1.43 | 1.10 | 1.09 |
| | | | non-image area | 0.08 | 0.09 | 0.10 |

TABLE 4

| | dye | developer | sensitizer | | dynamic color density | heat resistance | moisture resistance |
|---|---|---|---|---|---|---|---|
| Ex. 32 | 3-di-n-pentyl-amino-6-methyl-7-anilino-fluoran | condensation composition containing 55% of 2,2'-methylene-bis(4-t-butyl-phenol) | 1,2-di-(3-methyl-phenoxy)ethane | recorded area | 1.45 | 1.07 | 1.02 |
| | | | | non-image area | 0.08 | 0.09 | 0.10 |
| Ex. 33 | 3-di-n-butyl-amino-6-methyl-7-anilino-fluoran | condensation composition containing 55% of 2,2'-methylene-bis(4-t-butyl-phenol) | di-p-methyl-benzyl oxalate | recorded area | 1.42 | 1.09 | 1.06 |
| | | | | non-image area | 0.08 | 0.09 | 0.10 |
| Ex. 34 | 3-di-n-pentyl-amino-6-methyl-7-anilino-fluoran | condensation composition containing 55% of 2,2'-methylene-bis(4-t-butyl-phenol) | 1,2-bis-(phenoxy methyl)-benzene | recorded area | 1.40 | 0.98 | 1.00 |
| | | | | non-image area | 0.08 | 0.09 | 0.10 |
| Ex. 35 | 3-di-n-butyl-amino-6-methyl-7-anilino-fluoran | condensation composition containing 55% of 2,2'-methylene-bis(4-t-butyl-phenol) | 1,2-bis-(phenoxy methyl)-benzene | recorded area | 1.42 | 1.07 | 1.02 |
| | | | | non-image area | 0.08 | 0.09 | 0.10 |
| Ex. 36 | 3-di-n-pentyl-amino-6-methyl-7-anilino-fluoran + 3-di-n-butyl-amino-6-methyl-7-anilino-fluoran | condensation composition containing 55% of 2,2'-methylene-bis(4-t-butyl-phenol) | 1,2-bis-(phenoxy methyl)-benzene | recorded area | 1.45 | 1.13 | 1.10 |
| | | | | non-image area | 0.08 | 0.11 | 0.10 |

TABLE 5

| | dye | developer | sensitizer | | dynamic color density | heat resistance | moisture resistance |
|---|---|---|---|---|---|---|---|
| Ex. 37 | 3-di-n-butyl-amino-6-methyl-7-anilino-fluoran + 3-(N-ethyl-N-isoamyl-amino)-6-methyl-7-anilino fluoran | condensation composition containing 55% of 2,2'-methylene-bis(4-t-butyl-phenol) | 1,2-di-(3-methyl-phenoxy)ethane | recorded area | 1.46 | 1.10 | 1.05 |
| | | | | non-image area | 0.08 | 0.10 | 0.10 |
| Ex. 38 | 3-di-n-pentyl-amino-6-methyl-7- | condensation composition containing | di-p-methyl-benzyl | recorded area | 1.45 | 1.07 | 1.10 |
| | | | | non-image | 0.08 | 0.10 | 0.10 |

As shown in Tables 1–6, the thermal recording materials obtained using the developers (Examples 1–38) consisting of the composition of the present invention showed superior preservation stability while maintaining high dynamic color density. In contrast, when 2,2'-methylenebis(4-isopropylphenol) or 2,2'-methylenebis(4-t-butylphenol) alone was used as in Comparative Examples 1 and 2, the dynamic color density was low and the preservation stability was poor. In addition, the phenol novolac resins having high polymerization ratio as in Comparative Examples 3 and 4 showed very low dynamic color density, thus failing to afford satisfactory performance.

INDUSTRIAL APPLICABILITY

According to the present invention, a thermal recording material having high sensitivity and high dynamic color density, and superior in preservation stability can be obtained.

This application is based on patent application Nos. 2001-167233 and 2001-301577 filed in Japan, the contents of which are hereby incorporated by reference.

What is claimed is:

1. A thermal recording material comprising a support and a heat coloring layer formed thereon, which heat coloring layer consisting essentially of a developer and a basic dye, wherein said developer is comprised of condensates consisting of a condensate represented by the formula (I):

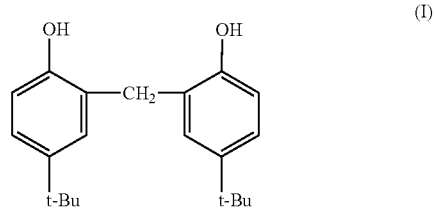

in a proportion of 40 to 90% based on the total of the condensates, and at least one condensate represented by the formula (II):

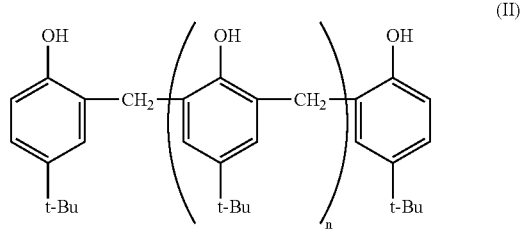

wherein n is an integer of 1 to 3.

* * * * *